United States Patent [19]

Metcalfe et al.

[11] Patent Number: 4,977,627
[45] Date of Patent: Dec. 18, 1990

[54] PROTECTIVE GOGGLE

[75] Inventors: Richard T. Metcalfe; Arthur J. Salce, both of Southbridge, Mass.

[73] Assignee: American Optical Corporation, Southbridge, Mass.

[21] Appl. No.: 259,171

[22] Filed: Oct. 18, 1988

[51] Int. Cl.5 ............................................. A61F 9/02
[52] U.S. Cl. .......................................... 2/437; 2/441; 2/447
[58] Field of Search .................... 2/437, 436, 426, 428, 2/429, 430, 431, 432, 434, 435, 438, 439, 440, 441, 452, 447

[56]  References Cited

U.S. PATENT DOCUMENTS

| | | | |
|---|---|---|---|
| 2,422,534 | 6/1947 | DuBois | 2/441 |
| 2,527,027 | 10/1950 | Mull | 351/44 X |
| 2,877,463 | 3/1959 | Watkins | 2/437 |
| 3,000,011 | 9/1961 | Sterne et al. | 2/436 |
| 3,027,562 | 4/1962 | Widenor | 2/430 |
| 3,395,406 | 8/1968 | Smith | 2/436 |
| 3,418,658 | 12/1968 | Danico | 2/436 |
| 3,517,393 | 6/1970 | Beauchef | 2/436 |
| 4,264,988 | 5/1981 | Specht | 2/431 |
| 4,468,819 | 9/1984 | Ohno et al. | 2/430 |
| 4,670,914 | 6/1987 | Harris | 2/436 |
| 4,689,838 | 9/1987 | Angermann et al. | 2/441 |
| 4,716,601 | 1/1988 | McNeal | 2/434 |

FOREIGN PATENT DOCUMENTS

| | | |
|---|---|---|
| 0699465 | 11/1953 | United Kingdom . |
| 0879077 | 10/1961 | United Kingdom . |
| 0921203 | 3/1963 | United Kingdom . |
| 0931850 | 7/1963 | United Kingdom . |

OTHER PUBLICATIONS

American Optical Safety Products Brochure (2 Sides); 1976.

Primary Examiner—Peter Nerbun
Attorney, Agent, or Firm—Fishman, Dionne & Cantor

[57] ABSTRACT

A flexible mask goggle is presented comprising a flexible housing which receives an optically transparent lens. The housing includes a novel ventilation structure along the upper and lower surfaces thereof. On the upper surface, this ventilation structure comprises an array of spaced slots while the ventilation structure on the lower surface comprises two spaced groups containing similar spaced slots. Both the upper and lower vents permit direct airflow in and out of the goggle. In an important feature of the present invention, removable caps are snap locked over the upper and lower ventilation structure. These caps convert the otherwise direct airflow through the vents to an indirect airflow.

42 Claims, 6 Drawing Sheets

PROTECTIVE GOGGLE

BACKGROUND OF THE INVENTION

This invention relates generally to protective goggles. More particularly, this invention relates to mask goggles which have a flexible lens housing and which include novel upper and lower ventilation sections. The goggles of this invention are particularly well suited for use as either an impact or chemical splash goggle; but may also be used as protective goggles for sporting applications.

Flexible mask goggles are well known and comprise a flexible (typically vinyl) shroud or housing which incorporates a substantially flat lens. When used as an impact goggle, the lens housing includes a plurality of spaced openings or holes along the top and/or sides for permitting direct ventilation into and out of the goggle interior. However, such impact goggles cannot be used as either splash or chemical goggles. This is because chemical goggles require indirect ventilation and splash goggles require peripheral indirect ventilation; neither of which are available from the plurality of spaced holes in the impact goggles. As a result, a goggle manufacturer must make and sell two or three different types of flexible mask goggles, all of which differ only in the ventilation structure. Of course, the necessity for all of these goggle types incur higher manufacturing and purchasing costs.

Still another drawback to the prior art flexible mask goggles is the flat lens. This lens has poor lateral and downward viewing areas resulting in undesired "tunnel vision".

SUMMARY OF THE INVENTION

The above-discussed and other drawbacks and deficiencies of the prior art are overcome or alleviated by the flexible mask goggle of the present invention. In accordance with the present invention, a flexible mask goggle is provided which comprises a flexible shroud or housing which receives an optically transparent lens. The housing includes a novel ventilation structure along the upper and lower surfaces thereof. On the upper surface, this ventilation structure comprises an array of spaced slots while the ventilation on the lower surface comprises two spaced groups or array containing similar spaced slots. It will be appreciated that both the upper and lower vents permit direct airflow in and out of the goggle.

In an important feature of the present invention, removable caps are snap locked over the upper and lower ventilation structure. This snap locking is accomplished through flexible hooked arms on the caps which are received through selected slots in the ventilation structure. These caps convert the otherwise direct airflow through the vents to an indirect airflow; and thus convert the application of the goggles from impact to chemical or splash. Thus, in accordance with the present invention, a single pair of flexible mask goggles can be used for both impact and chemical or splash applications with only the addition of small, inexpensive snap-on caps.

Another important feature of the present invention is the lens configuration which comprises a three section cylindrical lens consisting of two intersecting cylinder curves. This lens structure provides a significantly improved viewing area in both the frontal, downward and particularly lateral directions, as compared to the flat lens configuration of the prior art. As a result, the lens structure of this invention does not suffer from the "tunnel vision" of the prior art.

The above-discussed and other features and advantages of the present invention will be appreciated and understood by those of ordinary skill in the art from the following detailed description and drawings.

BRIEF DESCRIPTION OF THE DRAWINGS

Referring now to the drawings, wherein like elements are number alike in the several FIGURES.

DESCRIPTION OF THE PREFERRED EMBODIMENT

Figure 1:
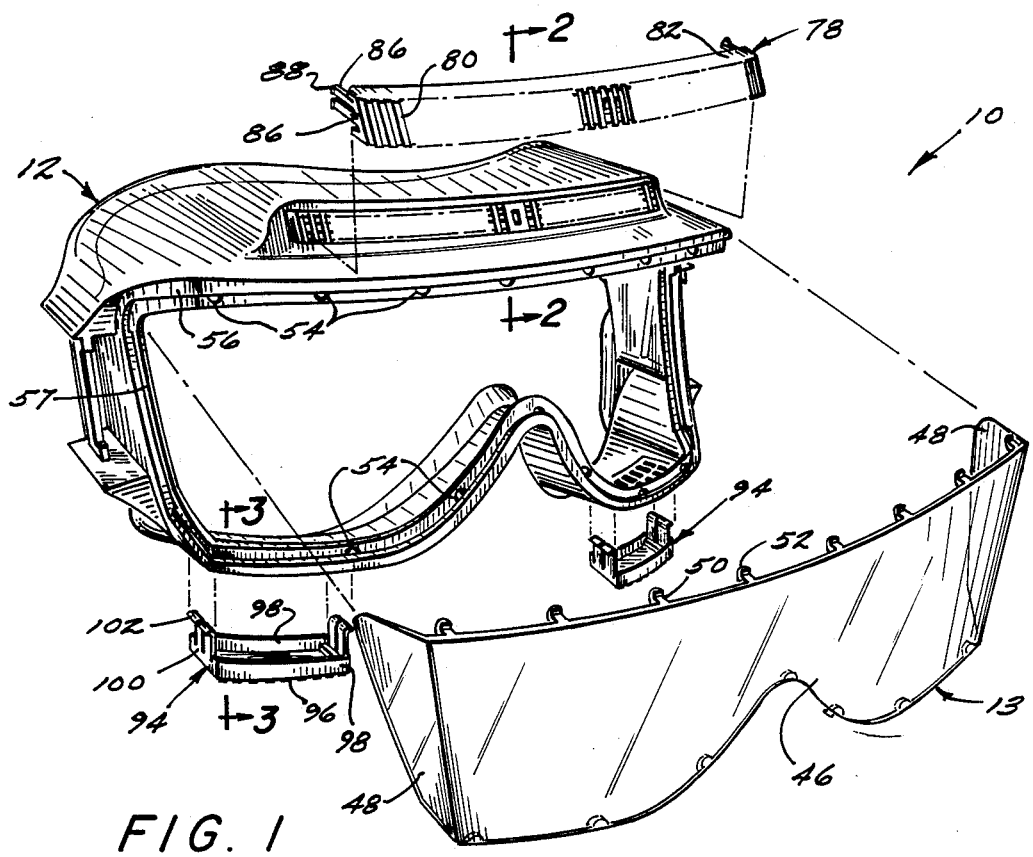
FIG. 1 is an exploded view of a flexible mask goggle in accordance with the present invention.

Referring initially to FIGS. 6-11, a pair of flexible mask goggles in accordance with a first embodiment of the present invention is shown generally at 10. Goggle 10 comprises a flexible (e.g. vinyl) shroud or housing 12 having a front opening for receiving and retaining a lens 13. Shroud 12 includes an upper portion 14, a pair of lateral or side portions 16 and 18 and a bottom portion 20. Upper portion 14 has a curved rearward surface 22 for effecting a snug fit on the forehead or brow of the wearer. Similarly, bottom portion 20 includes a rearward surface 24 and nose piece 25 which is adapted to effect a snug fit against the upper portion of the wearer's nose and cheeks. Upper portion 14 also includes a raised central area 14A which supports an upper ventilation section 26. Likewise, lower portion 20 also houses a pair of spaced lower ventilation sections 28. Rearward surface 22 of upper portion 14 includes a depending lip which is retained against the forehead of the wearer. Similar flexible lips are found along the side edges of rearward surface 24 and the two locations indicated at 30 on side portions 16 and 18.

Figure 8:
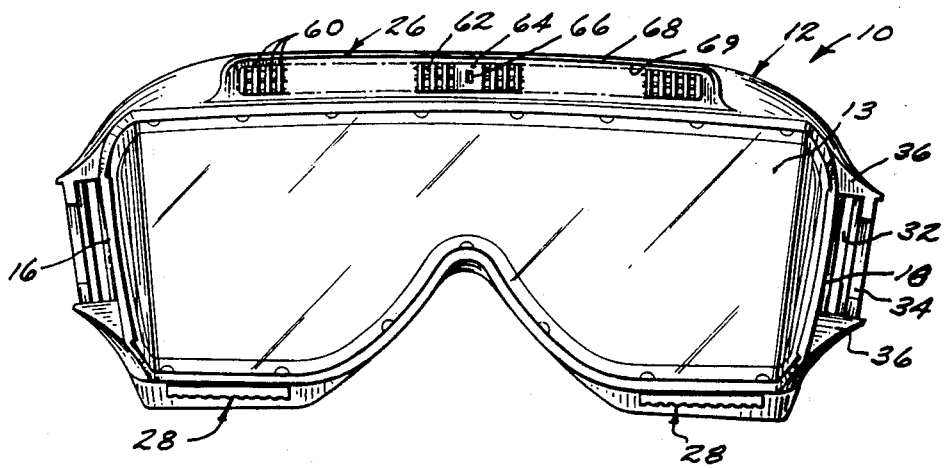
FIG. 8 is a front elevation view of the goggle of FIG. 6.
Figure 9:
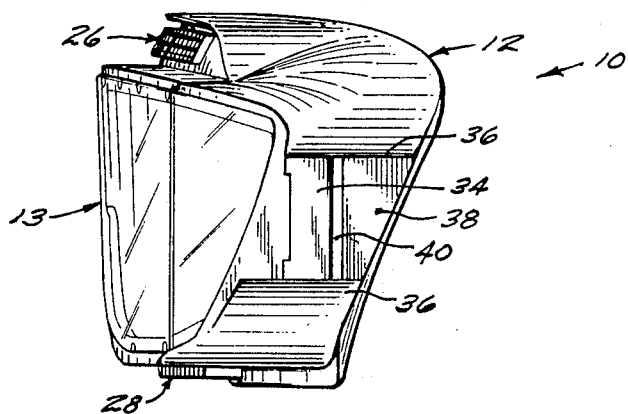
FIG. 9 is a side elevation view of the goggle of FIG. 6.
Figure 10:
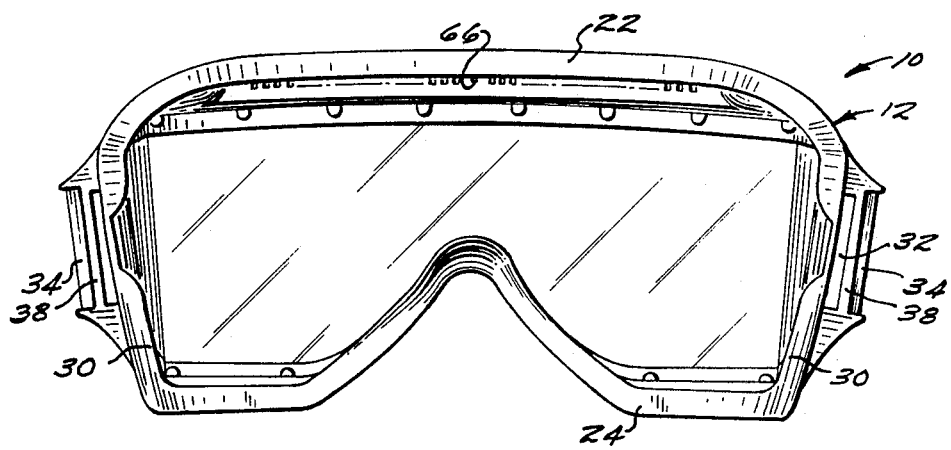
FIG. 10 is a rear view of the goggle of FIG. 6.

Large multiple headband slots 32 are located along the side sections 16 and 18 of goggle 10. Each slot 32 is defined by a longitudinal member 34 extending between a pair of transverse lateral arms 36. In addition, as shown in FIGS. 8 and 9, a second longitudinal member 38 is also positioned between laterally extending arms 36 to define slot 32. Second longitudinal member 38 is spaced back from member 34 to define there between groove 40. In this way, a strap may be threaded through slot 32, around member 34, through groove 40 and then back through slot 32 as shown in FIG. 9.

Referring now to FIG. 1, optically transparent (generally plastic) lens 13 is a novel three section cylindrical lens comprising two intersecting cylinder curves so as to define a front lens portion 46 and a pair of side lenses 48. This novel lens 13 offers an improved viewing area in the front direction and particularly in the lateral viewing area as compared to prior art flat lens goggles. In fact, the lens surface area of lens 13 has been increased by twenty-five percent in the forward area and approximately forty percent overall when compared to the prior art flat lens goggle. This increased lens size eliminates "tunnel vision" and restricted lateral viewing that is presently associated with existing flexible goggle lenses.

Lens retention to housing 12 is accomplished using a plurality (preferably 15) of rearwardly extending rigid arms 50 which terminate at small retaining hooks 52. These small locking arms 50 are received in a plurality of matching semi-circular openings 54 which extend completely through lens housing 12. It will be appreciated that locking arms 50 are sized to travel completely through lens housing openings 54 so that retaining hooks 52 will form a snug positive lock to the goggle housing structure. Such an attachment system not only provides a positive lens lock, but also allows flexibility in the goggle structure. In addition, a ridge 56 is provided along the entire periphery of housing 12 so that when lens 13 is locked into the lens housing 12, ridge 56 will support and be flush with lens 13. In side portions 16 and 18 of housing 12, ridge 56 cooperates with housing 12 to define a groove 57 which receives and fully surrounds and supports side lenses 48.

It will be appreciated that the rearwardly extending locking fingers 50 are designed to allow press molding without any secondary operations and therefore substantially lower the manufacturing and assembly costs of lens 13.

Figure 2:
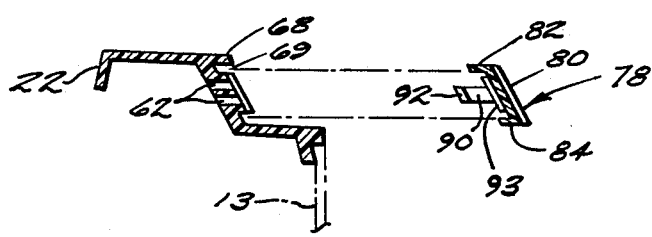
FIG. 2 is an exploded cross sectional elevation view along the lines 2—2 of FIG. 1.

As discussed, the present invention includes upper and lower ventilation portions 26 and 28. Referring to FIGS. 1 and 6-11, the upper ventilation portion comprises an array of slots or openings defined by a plurality of spaced parallel, vertical walls 58 which are intersected by three transverse sidewalls 60. It will be appreciated that walls 60 run essentially horizontal and perpendicular to vertical walls 58. Also, as will be discussed hereinafter, walls 60 have a slightly lower height than walls 58. Together, walls 58 and 60 define an array of openings 62 having two rows. Openings 62 are sized to allow for air passage through the inside of the goggle, but are small enough to restrict objects from entering. Openings 62 extend longitudinally as seen in FIG. 2. At about the center of the array of openings is a square area denoted by the numeral 64 having a rectangular opening 66 therethrough. A flexible flap or extension 68 is spaced from the ventilation section 26 and defines a small gap 69 therebetween.

Figure 11:
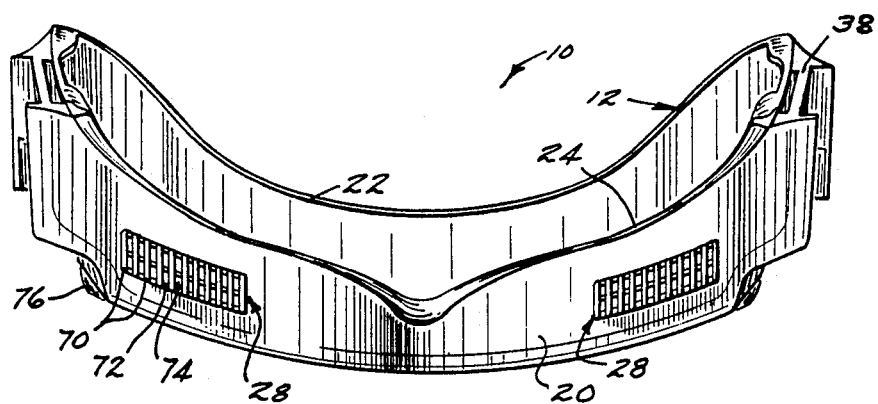
FIG. 11 is a bottom view of the goggle of FIG. 6.
Figure 12:
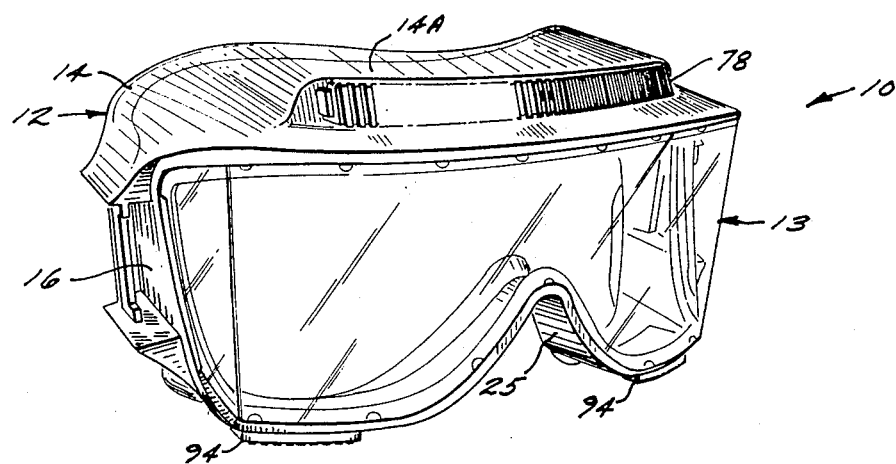
FIG. 12 is a perspective front elevation view of a flexible mask goggle in accordance with a second embodiment of the present invention.
Figure 13:
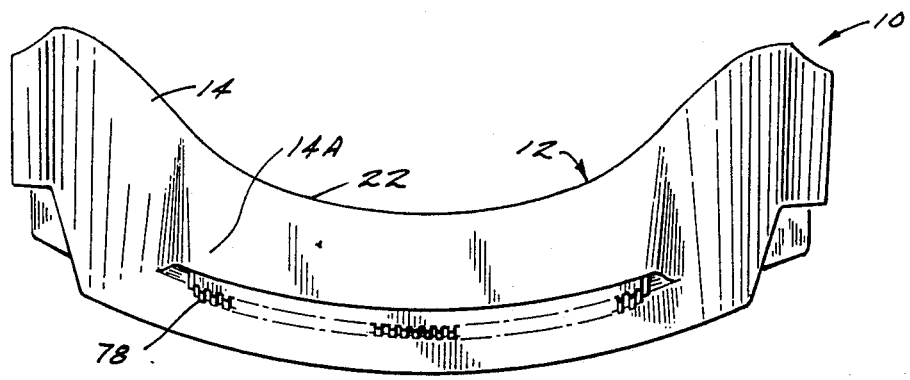
FIG. 13 is a plan view of the goggle of FIG. 12.
Figure 14:
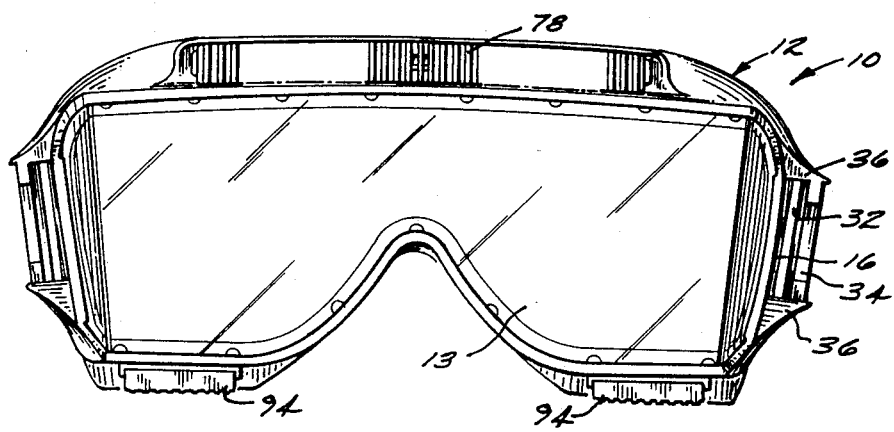
FIG. 14 is a front elevation view of the goggle of FIG. 12.
Figure 15:
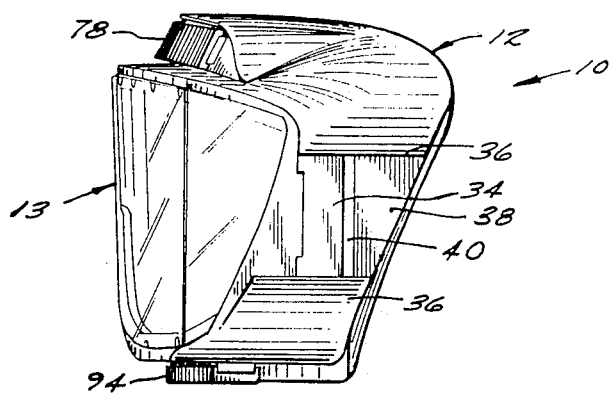
FIG. 15 is an end view of the goggle of FIG. 12.
Figure 16:
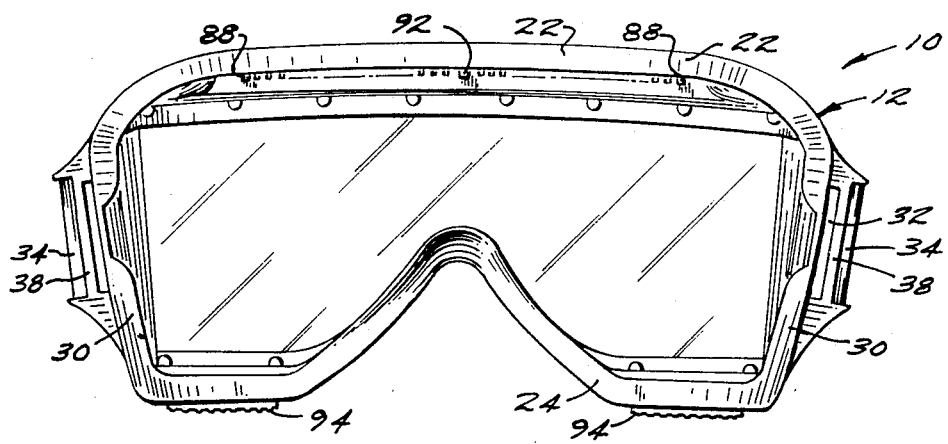
FIG. 16 is a rear view of the goggle of FIG. 12.
Figure 17:
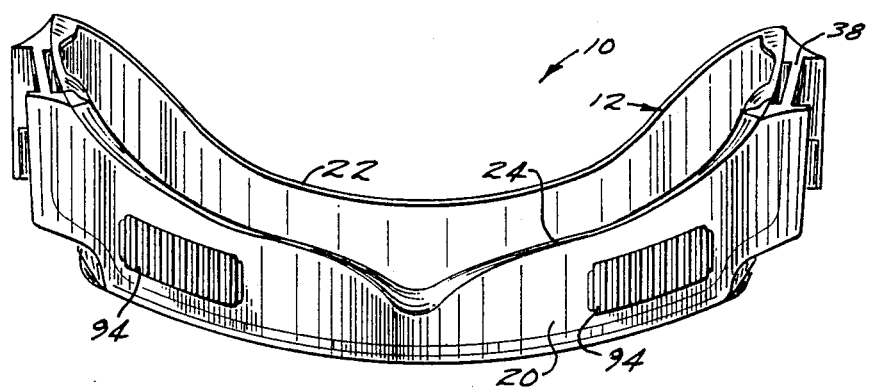
FIG. 17 is a bottom view of the goggle of FIG. 12.

Goggle 10 also includes a pair of lower ventilation ports 28 on lower portion 20 of housing 12 (see FIG. 11). Each ventilation section 28 is substantially similar to upper ventilation section 26 and is thus comprised of a plurality of parallel spaced walls 70 intersected by three spaced transverse walls 72 to define two rows of openings 74. Also, as in upper ventilation section 26, in lower ventilation sections 28, walls 70 have a height which are somewhat larger than walls 72.

The flexible mask goggle of FIGS. 6-11 thus has ventilation sections 26 and 28 which afford direct passage of air into and out of the goggle. This feature makes goggle 10 well suited for use where impact protection is needed. In addition, the goggle depicted in FIGS. 6-11 may also be used in other sporting applications such as skiing and racquet sports.

Referring now to FIGS. 1-5 and 12-17, an important feature of the present invention is the presence of removable snap-on caps 78 and 94 which convert the direct ventilation holes 60 and 76 to indirect ventilation holes. This is accomplished in upper ventilation section 26 by an upper snap-on cap 78. Vent cap 78 is preferably one-piece molded plastic and has an aesthetically pleasing outside surface consisting of alternating hills and valleys shown at 80. Cap 78 has a pair of opposed upper and lower side walls 82 and 84 which define a U-shape together with the front undulating section 80. The opposed ends of ventilation caps 78 each have a pair of flexible arms 86 which terminate at a hook portion 88. Each pair of arms 86 is sized and spaced so as to be received in an opposed pair of openings 60 in the array of openings of ventilation section 26. Thus, when cap 78 is aligned with ventilation section 26, resilient arms 86 are forced through the appropriate opening 60 until hook portions 88 snap through and are retained by housing portion 12. In addition, cap 78 includes a central arm 90 which terminates in a flat rectangular member 92. It will be appreciated that when cap 78 is attached to ventilation portion 26, arm 90 will be forced through opening 66 so that rectangular head 92 of arm 90 will snap through opening 66 and be retained by housing 12. The inside surface of cap 78 includes a plurality of stand-offs 93 which acts to step cap 78 away from upper ventilation portion 26.

Similarly, lower ventilation sections 28 each receive a lower protective insulation cap 94 which has a front ridged surface 96 and a pair of depending side surfaces 98 which together define a U-shaped cross section. Each cap 94 also includes opposed pairs of resilient finger elements 100 which terminate at hooks 102. Resilient members 100 and hooks 102 are forced through openings 76 of lower ventilation portions 28 to form a snug snap lock therewith. Like upper ventilation cap 78, lower ventilation caps 94 includes a plurality of stand-offs 103 (see FIG. 5B) for stepping caps 94 away from lower ventilation portions 28.

Figure 3:
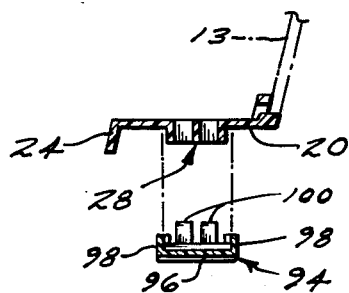
FIG. 3 is an exploded cross sectional elevation view along the line 3—3 of FIG. 1.
Figure 3A:
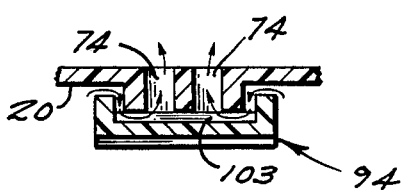
FIG. 3A is a cross sectional assembled view similar to the view of FIG. 3.
Figure 4B:
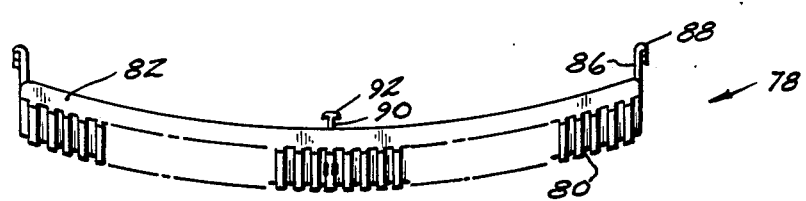
FIG. 4B is a top elevation view of the cap of FIG. 4A.
Figure 4A:
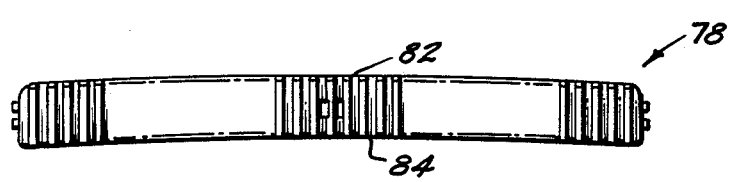
FIG. 4A is a front elevation view of the upper cap for snap locking onto the goggle of FIG. 1.
Figure 4C:
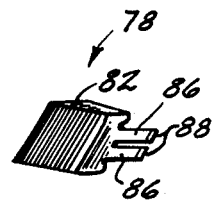
FIG. 4C is a side elevation view of the cap of FIG. 4A.
Figure 5B:
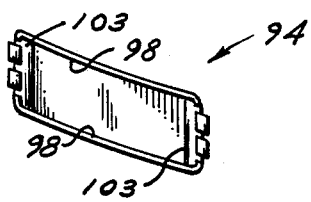
FIG. 5B is a plan interior view of the cap of FIG. 5A.
Figure 5A:
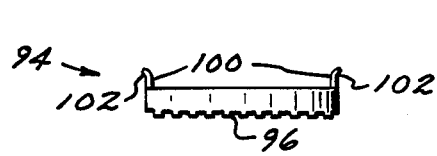
FIG. 5A is a front elevation view of a lower cap which is snap locked onto the goggle of FIG. 1.
Figure 5C:
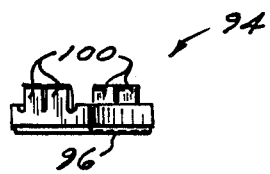
FIG. 5C is a side perspective view of the cap of FIG. 5A.
Figure 6:
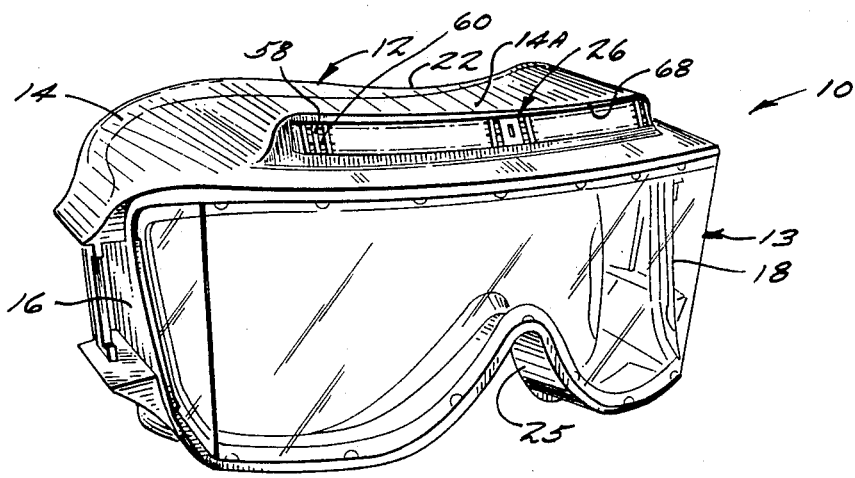
FIG. 6 is a perspective front elevation view of a flexible mask goggle in accordance with a first embodiment of the present invention.
Figure 7:
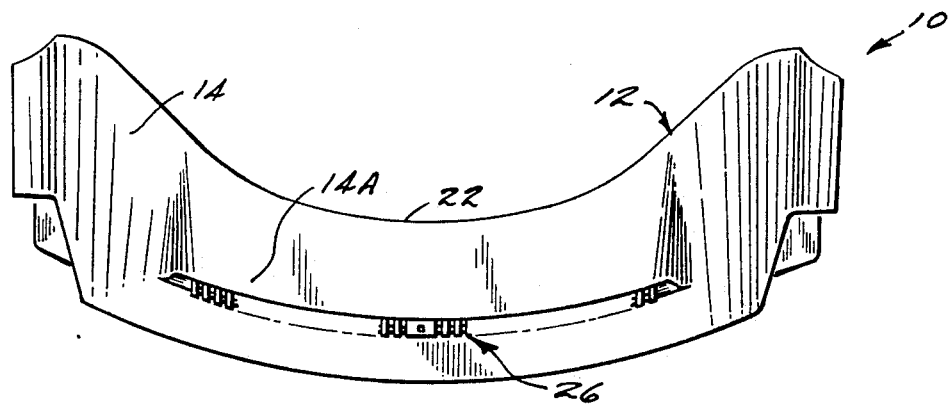
FIG. 7 is a plan view of the goggle of FIG. 6.

In applications where splash and chemical protection is a requirement, the protective ventilation caps 78 and 94 can be easily installed onto upper and lower ventilation sections 26 and 28. When in place, the ventilation caps 78 and 94 will provide splash protection and also provide an indirect path for air circulation. This indirect path is clearly shown in the cross sectional FIG. 3A and results from the stand-offs 93 and 103 precluding the caps 78 and 94, respectively from fully closing the vents. Thus, by virtue of the stand-offs, air is allowed to circulate around the top and bottom sides of the caps. It will be appreciated that the gap 70 defined by outwardly extending ridge 68 will receive upper surface 82 of cap 78 so as to cover the top portion of this upper vent cap. This overhead flap 68 will thus provide additional protection from overhead splashes and prevent liquids from entering the indirect ventilation path.

The protective goggles of the present invention provide many important features and advantages over prior art protective goggles. An important feature is that the addition of ventilation caps 78 and 94 will convert the protective goggles (of FIGS. 6-11) from use merely in impact applications to use in splash protection and chemical protection (FIGS. 12-17). This is an important feature over the prior art wherein separate goggles had to be manufactured for either impact uses or chemical and splash uses. Thus, a single housing 12 and lens 13 may be used for either impact or chemical and splash applications with only the necessity of providing the relatively inexpensive caps 78 and 94 for conversion from impact to splash or chemical uses. This leads to far lower manufacturing and purchasing costs relative to the prior art.

Still another important feature of the present invention is the use of novel lens 13 which is comprised of a three-section cylindrical configuration. This lens substantially increases the viewing area in both the forward and lateral directions relative to the flat lens products of the prior art and eliminates the "tunnel vision" drawback associated with the prior art goggles.

The housing 12 of the present invention also incorporates pantoscopic angle design which allows exceptional viewing in the forward and down positions and which was not present in prior art flat lens goggles. The housing configuration allows the housing to fit the wearer more comfortably while also placing or orienting the lens at the proper attitude in front of the wearer's eyes.

In addition, the interior recess defined by outwardly extending section 14A of housing 12 provides the necessary clearance to permit the wearing of spectacle temples by the wearer of the goggles.

It will be appreciated that while a preferred embodiment of the present invention utilizes a lens 13 having two intersecting cylinder curves, the present invention also contemplates the use of a conventional flat or spherical lens surface on the side panels intersecting the front lens portion.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A protective goggle comprising:
    a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;
    a lens having attaching means for attaching to said front opening of said housing;
    an upper ventilation section on said upper surface of said housing, said upper ventilation section comprising an array of upper openings for providing direct ventilation; and
    at least one lower ventilation section on said lower surface of said housing, said lower ventilation section comprising an array of lower openings for providing direct ventilation;
    wherein said array of upper and lower openings define a plurality of adjacent and aligned columns and rows of openings formed by a plurality of spaced first wall members and at least one second wall member transverse to said first wall members, said first and second wall members defining said upper or lower openings, at least some of said first wall members having heights which differ from said second wall member.

2. The goggle of claim 1 including:
    an upper ventilation cap attachable over said upper ventilation section, said upper ventilation cap including means for providing indirect ventilation through said upper openings; and
    a lower ventilation cap attachable over said lower ventilation section, said lower ventilation cap including means for providing indirect ventilation through said lower openings.

3. The goggle of claim 1 wherein:
    said upper ventilation cap includes resilient arm means terminating at first locking means, said arm means being received in corresponding upper openings wherein said first locking means locks said upper ventilation cap to said housing upper surface; and
    said lower ventilation cap includes resilient arm means terminating at second locking means, said arm means being received in corresponding lower openings wherein said second locking means locks said lower ventilation cap to said housing lower surface.

4. The goggle of claim 3 wherein said upper ventilation section includes a central opening and wherein:
    said upper ventilation cap further includes a central member extending therefrom and terminating at third locking means, said central member being received in said central opening to further lock said upper ventilation cap to said housing upper surface.

5. The goggle of claim 2 wherein each of said upper and lower ventilation caps comprise:
    a top surface and a pair of opposed side surfaces defining an approximate U-shaped cross section.

6. The goggle of claim 5 wherein:
    said top surface has an undulating configuration.

7. The goggle of claim 2 wherein:
    said upper surface of said housing includes a flexible flap extending outwardly therefrom, said flap being spaced from said upper ventilation section to define a gap between said flap and said upper ventilation section.

8. The goggle of claim 7 wherein:
    a portion of said upper ventilation cap is inserted in said gap between said flap and said upper ventilation section.

9. The goggle of claim 2 wherein said means for providing indirect ventilation includes:

stand-off means on said caps for preventing said caps from closing said ventilation sections wherein said stand-off means interacts with said first and second wall members to provide an indirect ventilation path between said caps and said ventilation sections.

10. The goggle of claim 1 wherein:
said housing upper surface has a raised central area defining an interior recess, said upper ventilation section forming a portion of said raised central area.

11. The goggle of claim 1 wherein:
said lens includes a front portion and a pair of opposed side portions extending laterally from said front portion.

12. The goggle of claim 11 wherein:
said front portion and opposed side portions comprise two intersecting cylindrical curves.

13. The goggle of claim 11 wherein said attaching means comprises:
a plurality of spaced hooked protrusions extending outwardly from the periphery of said lens; and
a plurality of matching holes along the periphery of said front opening of said housing, said hooked protrusions being received by said holes to lock said lens to said housing.

14. The goggle of claim 13 including:
a ridge surrounding and spaced from said front opening of said housing, said lens abutting said ridge and said lens being approximately flush with said ridge.

15. The goggle of claim 11 wherein each of said side surfaces of said housing terminate at said front opening of said housing at a groove and wherein:
said opposed side portions of said lens are received and retained by said grooves.

16. The goggle of claim 1 including:
a pair of spaced lower ventilation sections on said lower surface of said housing.

17. The goggle of claim 1 including:
strap retaining means on each of said side surfaces of said housing.

18. The goggle of claim 17 wherein said strap retaining means comprises:
a pair of spaced lateral members extending from said side surfaces;
a first substantially vertical member between said lateral members and spaced from side surfaces.

19. The goggle of claim 18 including:
a second substantially vertical member between said lateral members and spaced from both said first vertical member and said side surfaces, said first vertical member having a different height than said second vertical member.

20. A protective goggle comprising:
a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;
a lens having attaching means for attaching to said front opening of said housing;
at least one ventilation section on said housing, said ventilation section comprising an array of openings for providing direct ventilation, said array of openings defining a plurality of adjacent and aligned columns and rows of openings;
wherein said ventilation section comprises;
a plurality of spaced first wall members; and
at least one second wall member transverse to said first wall members, said first and second wall members defining said array of openings, at least some of said first wall members having heights which differ from said second wall member.

21. The goggle of claim 20 including:
a ventilation cap attachable over said ventilation section, said ventilation cap including means for providing indirect ventilation through said openings.

22. The goggle of claim 21 wherein:
said ventilation cap includes resilient arm means terminating at first locking means, said arm means being received in corresponding of said openings wherein said first locking means locks said ventilation cap to said housing.

23. The goggle of claim 21 wherein said ventilation cap comprises:
a top surface and a pair of opposed side surface defining an approximate U-shape cross section.

24. The goggle of claim 23 wherein:
said top surface has an undulating configuration.

25. The goggle of claim 21 wherein said means for providing indirect ventilation includes:
stand-off means on said cap for preventing said cap from closing said ventilation section wherein said standoff means interacts with said first and second wall members to provide an indirect ventilation path between said cap and said ventilation section.

26. The goggle of claim 20 wherein:
said lens includes a front portion and a pair of opposed side portions extending laterally from said front portion.

27. The goggle of claim 25 wherein:
said front portion and opposed side portions comprise two intersecting cylindrical curves.

28. The goggle of claim 27 wherein said attaching means comprises:
a plurality of spaced hooked protrusions extending outwardly from the periphery of said lens; and
a plurality of matching holes along the periphery of said front opening of said housing, said hooked protrusions being received by said holes to lock said lens to said housing.

29. The goggle of claim 28 including:
a ridge surrounding and spaced from said front opening of said housing, said lens abutting said ridge and said lens being approximately flush with said ridge.

30. The goggle of claim 27 wherein each of said side surfaces of said housing terminate at said front opening of said housing at a groove and wherein:
said opposed side portions of said lens are received and retained by said grooves.

31. A protective goggle comprising:
a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;
a lens having attaching means for attaching to said front opening of said housing;

an upper ventilation section on said upper surface of said housing, said upper ventilation section comprising an array of upper openings for providing direct ventilation wherein said upper openings extend longitudinally in a particular direction, said upper surface of said housing including an integral flexible flap extending outwardly therefrom and in said direction parallel to said upper openings, said flap being spaced from said upper ventilation section to define a gap between said flap and said upper ventilation section; and at least one lower ventilation section on said lower surface of said housing, said lower ventilation section comprising an array of lower openings for providing direct ventilation.

32. The goggle of claim 31 including:

an upper ventilation cap attachable over said upper ventilation section, said upper ventilation cap including means for providing indirect ventilation through said upper openings; and a lower ventilation cap attachable over said lower ventilation section, said lower ventilation cap including means for providing indirect ventilation through said lower openings.

33. The goggle of claim 32 wherein:

a portion of said upper ventilation cap is inserted in said gap between said flap and said upper ventilation section.

34. A protective goggle comprising:

a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;

a lens having attaching means for attaching to said front opening of said housing;

an upper ventilation section on said upper surface of said housing, said upper ventilation section comprising an array of upper openings for providing direct ventilation; and at least one lower ventilation section on said lower surface of said housing, said lower ventilation section comprising an array of lower openings for providing direct ventilation;

strap retaining means on each of said side surfaces of said housing, said strap retaining means comprising;

a pair of spaced lateral members extending from said side surfaces;

a first substantially vertical member between said lateral members and spaced from said side surfaces; and a second substantially vertical member between said lateral members and spaced from both said first vertical member and said side surfaces, said first vertical member having a different height than said second vertical member.

35. A protective goggle comprising:

a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;

a lens having attaching means for attaching to said front opening of said housing, said lens comprising three distinct and discrete lens portions including a front lens portion and a pair of opposed side lens portions extending laterally from said front lens portion, said front lens portion and opposed side lens portions comprising two intersecting cylindrical curves;

an upper ventilation section on said upper surface of said housing, said upper ventilation section comprising an array of upper openings for providing direct ventilation; and at least one lower ventilation section on said lower surface of said housing, said lower ventilation section comprising an array of lower openings for providing direct ventilation.

36. The goggle of claim 35 wherein:

said front lens portion and opposed side lens portions comprise two intersecting cylindrical curves.

37. A protective goggle comprising:

a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;

a lens having attaching means for attaching to said front opening of said housing said lens comprising three distinct and discrete lens portions including a front lens portion and a pair of opposed side lens portions extending laterally from said front lens portion;

at least one ventilation section on said housing, said ventilation section comprising an array of openings for providing direct ventilation, said array of openings defining a plurality of adjacent and aligned columns and rows of openings.

38. The goggle of claim 37 wherein:

said front lens portion and opposed side lens portions comprise two intersecting cylindrical curves.

39. A protective goggle comprising:

a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;

a lens having attaching means for attaching to said front opening of said housing;

an upper ventilation section on said upper surface of said housing, said upper ventilation section comprising an array of upper openings for providing direct ventilation; and at least one lower ventilation section on said lower surface of said housing, said lower ventilation section comprising an array of lower openings for providing direct ventilation;

wherein said attaching means comprises;

a plurality of spaced hooked protrusions extending outwardly and transversely from the periphery of said lens; and a plurality of matching holes along the periphery of said front opening of said housing, said hooked protrusions being received by said holes to lock said lens to said housing.

40. The goggle of claim 39 including:

a ridge surrounding and spaced from said front opening of said housing, said lens abutting said ridge and said lens being approximately flush with said ridge.

41. A protective goggle comprising:

a housing, said housing having an upper surface, a lower surface and a pair of opposed side surfaces which together define a front opening and a rear opening, said upper surface having a rearward surface adapted to conform to the brow of a wearer and said lower surface having a rearward surface adapted to conform to the cheeks and nose of a wearer;

a lens having attaching means for attaching to said front opening of said housing;

at least one ventilation section on said housing, said ventilation section comprising an array of openings for providing direct ventilation, said array of openings defining a plurality of adjacent and aligned columns and rows of openings;

wherein said attaching means comprises;

a plurality of spaced hooked protrusions extending outwardly and transversely from the periphery of said lens; and a plurality of matching holes along the periphery of said front opening of said housing, said hooked protrusions being received by said holes to lock said lens to said housing.

42. The goggle of claim 41 including:

a ridge surrounding and spaced from said front opening of said housing, said lens abutting said ridge and said lens being approximately flush with said ridge.

* * * * *